(12) United States Patent
Kauppinen

(10) Patent No.: US 7,738,116 B2
(45) Date of Patent: Jun. 15, 2010

(54) PHOTOACOUSTIC DETECTOR

(75) Inventor: Jyrki Kauppinen, Ilmarinen (FI)

(73) Assignee: Gasera Ltd., Turku (FI)

( * ) Notice: Subject to any disclaimer, the term of this patent is extended or adjusted under 35 U.S.C. 154(b) by 308 days.

(21) Appl. No.: 10/529,597

(22) PCT Filed: Sep. 19, 2003

(86) PCT No.: PCT/FI03/00684

§ 371 (c)(1),
(2), (4) Date: Dec. 29, 2005

(87) PCT Pub. No.: WO2004/029594

PCT Pub. Date: Apr. 8, 2004

(65) Prior Publication Data

US 2006/0126070 A1    Jun. 15, 2006

(30) Foreign Application Priority Data

Sep. 30, 2002    (FI) .................................. 20021733

(51) Int. Cl.
*G01B 11/02* (2006.01)
(52) U.S. Cl. .................. 356/502; 356/501; 356/498
(58) Field of Classification Search ................ 356/432, 356/502; 359/285; 73/715
See application file for complete search history.

(56) References Cited

U.S. PATENT DOCUMENTS 3,471,238 A * 10/1969 Hawke .................. 356/486
4,355,234 A    10/1982 Fertig et al.
4,557,603 A    12/1985 Oehler et al.
4,996,627 A    2/1991 Zias et al.

(Continued)

FOREIGN PATENT DOCUMENTS

EP    0 389 071 A2    9/1990

(Continued)

OTHER PUBLICATIONS

Ledermann, Nicolas et al., "Piezoelectric Cantilever Microphone for Photoacoustic Gas Detector," *Integrated Ferroelectrics*, 2001, pp. 177-184, vol. 35, OPA (Overseas Publishers Association) N. V.

(Continued)

*Primary Examiner*—Gregory J Toatley, Jr.
*Assistant Examiner*—Jonathon D Cook
(74) *Attorney, Agent, or Firm*—Buchanan Ingersoll & Rooney PC

(57) ABSTRACT

The invention relates to a photoacoustic detector, comprising at least a first chamber ($V_0$) suppliable with a gas to be analyzed, a window for letting modulated and/or pulsed infrared radiation and/or light in the first chamber ($V_0$), and means for detecting pressure variations created in the first chamber by absorbed infrared radiation and/or light. The means for detecting pressure variations created in the first chamber by absorbed infrared radiation and/or light comprise at least an aperture provided in the wall of the first chamber ($V_0$), in communication with which is provided a door arranged to be movable in response to the movement of a gas, and means for a contactless measurement of the door movement. The invention relates also to a sensor for a photoacoustic detector and to a method in the optimization of a door used as a sensor for a photoacoustic detector.

11 Claims, 6 Drawing Sheets

U.S. PATENT DOCUMENTS

Figure 4A:
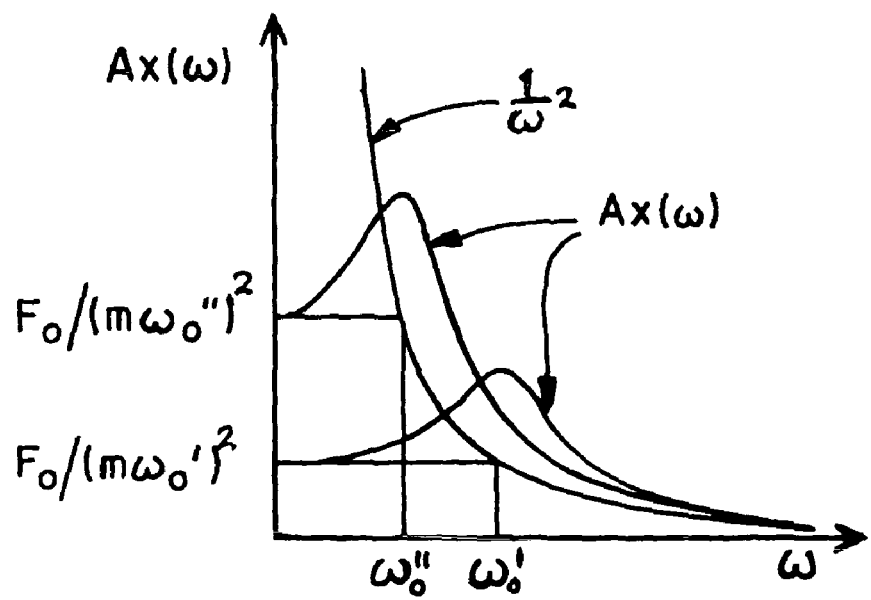

| | | | |
|---|---|---|---|
| 5,032,026 A * | 7/1991 | Jouve et al. | 356/478 |
| 5,629,757 A * | 5/1997 | Sakata | 356/35.5 |
| 6,082,178 A | 7/2000 | Bernstein et al. | |
| 6,222,190 B1 | 4/2001 | Bernstein et al. | |
| 6,474,168 B1 * | 11/2002 | Meringdal | 73/715 |

FOREIGN PATENT DOCUMENTS

| | | |
|---|---|---|
| EP | 1 211 501 A1 | 6/2002 |
| EP | 1 239 698 A1 | 9/2002 |
| WO | 95/34917 A1 | 12/1995 |
| WO | 03/046498 A1 | 6/2003 |

OTHER PUBLICATIONS de Paula, M.H. et al., "Optical microphone for photoacoustic spectroscopy," *J. Appl. Phys.*, Oct. 1, 1988, pp. 3722-3724, vol. 64, No. 1, American Institute of Physics.

de Paula, M.H., et al., "High-sensitivity optical microphone for photoacoustics," *Rev. Sci. Instrum*, Jun. 1992, pp. 3487-3491, vol. 63, No. 6, American Institute of Physics.

\* cited by examiner

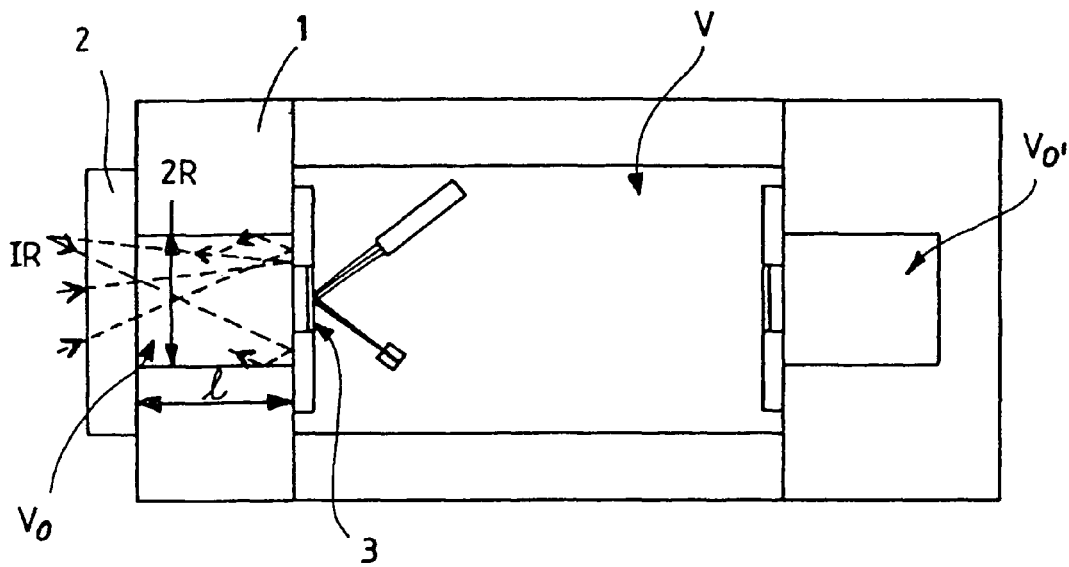
FIG. 1
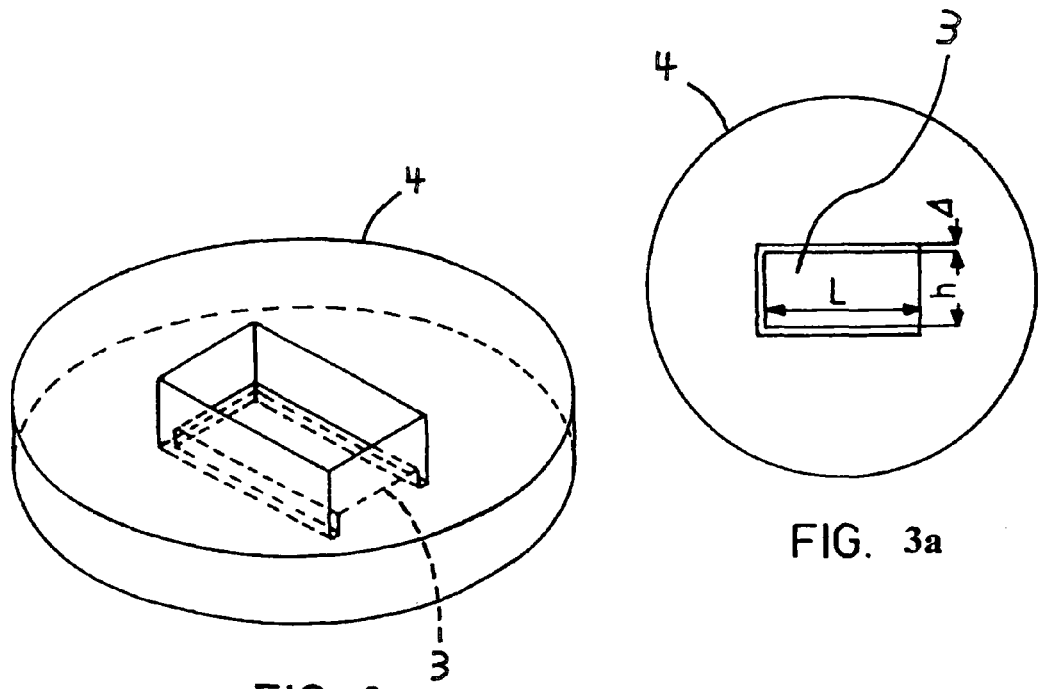
FIG. 2
FIG. 3a
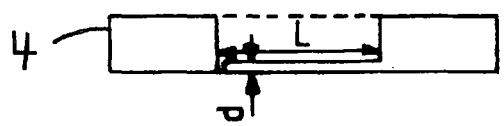
FIG. 3b

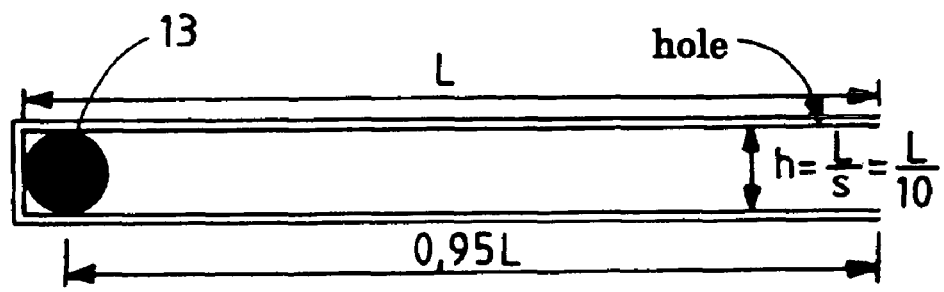
FIG. 11
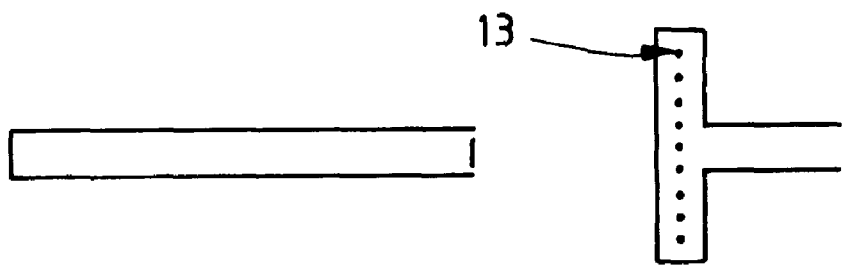
FIG. 12a
FIG. 12b
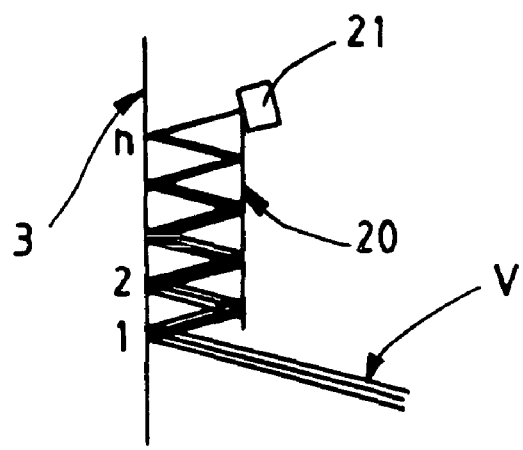
FIG. 13

PHOTOACOUSTIC DETECTOR

FIELD OF THE INVENTION

The invention relates to a photoacoustic detector as set forth in the preambles of the appended independent claims, and to a sensor for a photoacoustic detector as well as to a method in the optimization of a door used as a sensor for a photoacoustic detector.

DESCRIPTION OF RELATED ART

When infrared radiation or light in general falls on a gas-filled chamber containing a gas to be analyzed at a partial pressure $p_x$ and a carrier gas at a partial pressure $p_N$ (often typically nitrogen), radiation will be absorbed by the gas $p_x$. After the absorption process, energy converts to thermal movement at a certain time constant $\tau$ (e.g. $10^{-5}$ s). Thus, temperature of the total gas increases by $\Delta T$ per unit time. The increase of temperature results also in a pressure increase $\Delta p$.

A typical photoacoustic detector comprises a chamber, which is suppliable with a gas to be analyzed, a window for letting modulated or pulsed infrared radiation or light in the chamber, and a pressure sensor adapted to measure pressure variations produced by absorbed infrared radiation or light in the chamber. The pressure sensor comprises typically a microphone, a thin Mylar or metal film. A photoacoustic detector can be used for measuring or detecting infrared radiation in general, but one specific and important application of a detector deals with the measurement and detection of gases or gas mixtures regarding for example air quality and pollution.

In microphones, the movement of a film (Mylar) is usually measured capacitively. The Mylar film is coated with metal and placed in the proximity of another solid metal diaphragm. The result is a capacitor, having a capacitance $$C = \frac{\varepsilon_r \varepsilon_0 A}{h}, \tag{a}$$

where h represents a distance between the films at rest, A is a surface area of the films, $\varepsilon_r \varepsilon_0$ is a dielectric constant for a gas present between the sheets and $\varepsilon_0$ the same for a vacuum. The measurement of C provides h which gives the movement of a Mylar film, because $$\Delta C = -\frac{\varepsilon_r \varepsilon_0 A}{3h^2} \Delta h, \tag{b}$$

where $\Delta h$ is a change of distance in the middle and $\Delta h/3$ is an average change of distance. Further $$\frac{\Delta C}{C} = -\frac{\Delta h}{h} \tag{c}$$

or $$|\Delta h_{min}| \approx \frac{h}{C/\Delta C} = \frac{h}{S/N}, \tag{d}$$

where S/N is a signal-to-noise ratio in measuring electronics.

Capacity measurements of the prior art are limited by a gas flow present between the sheets, as h changes. As the gap h decreases, the gas is forced to flow out from between the sheets and return when h is increasing. The flow has inertia and that requires energy. A result of this is that, the higher the angular oscillation frequency $\omega$ of a diaphragm and the smaller h, the more the flow decreases the amplitude of a diaphragm movement. Thus, h cannot be decreased infinitely, as this would augment a signal $\Delta C$. Therefore, the commercially available microphones function at the limits of physical laws and their responsivity cannot be improved in that regard.

In their publication [1], Nicolas Lederman et al. disclose a photoacoustic detector for a sensor, wherein the sensor is fabricated from a cantilever type film, which responses to the movement of a gas in the chamber of a photoacoustic detector and in which film is integrated a piezoelectric element registering the cantilever movement. A problem with the sensor set forth in the publication is that the cantilever's resonance frequency has been omitted. It is likely that a piezoelectric element attached to a sensor increases the sensor's resonance frequency and thus deteriorates the sensor's response. The sensor presented in the publication is quite inaccurate and, therefore, not suitable for high precision applications. Neither does the publication say anything about optimization of a chamber and a sensor in the photoacoustic detector, i.e. the ratio of the size of a chamber to that of a sensor.

In their publications [2] and [3], M. H. de Paula et al. also disclose an alternative to a traditional diaphragm solution. The publications propose that a pellicle be fitted over a small duct in a photoacoustic detector cell at a distance of about 0.1 mm from the duct. According to what is stated in the publication, the pellicle is not provided with a so-called rim around itself, the pellicle thus extending beyond the duct boundaries, i.e. the question is not about a cantilever like the one shown in publication [1]. Hence, the fundamental problem in the publications of de Paula et al. is indeed the fact that the pressure to be measured and existing in a photoacoustic detector cell is only applied to a small portion of the total area of the pellicle, resulting in a considerably lower response. In addition, there is a leak from under the pellicle which is large with respect to the duct size, which further reduces the pellicle response. The publications [2] and [3] further describe an optical angular measurement for measuring the movement of a pellicle. However, the shape of a pellicle set forth in the cited publications is in practice unfavourable for angular measuring. Consequently, the solution proposed in publications [2] and [3] is not sufficiently responsive for highly accurate measurements and high precision applications.

Furthermore, atomic force microscopy uses cantilever typed pellicles. High frequencies are thus required from the pellicles, and, therefore, pellicles used in atomic force microscopy are not suitable for a photoacoustic detector.

Another problem in photoacoustic detection is a disturbance thereof as a result of external sounds. Thus, if the intra-chamber sound, infiltrated from outside the measuring instrument, is more powerful than the intrinsic noise of a system, the improvement regarding the sensitivity (response) of a detector system does not improve the determination of a gas to be analyzed. A typical method for reducing disturbances created by external sounds is sound proofing. Proofing is capable of damping external sounds at a coefficient of 10000-100000.

Another prior known means of reducing disturbances caused by external sounds comprises the use of double detection for a partial reduction of interfering sounds. In prior known double detection systems, a measuring system is provided which is identical to the regular measuring system, said identical system being denied the access of light, and it only measures sound within the chamber. Then, according to the solutions of prior art systems, there is performed a direct amplification of the difference between the actual measuring signal and a reference signal given by the identical measuring system. However, a problem with double detection systems as described above is e.g. that these systems only function in a special situation over a narrow frequency band. The problem is due to a phase difference created between sensors in the measuring systems.

SUMMARY

Consequently, it is an object of the photoacoustic detector, the sensor for the photoacoustic detector and the method in the optimization of a door used as a sensor for the photoacoustic detector, in accordance with the invention, to eliminate or at least alleviate the above-described prior art problems.

Another object of the photoacoustic detector, the sensor for the photoacoustic detector and the method in the optimization of a door used as a sensor for the photoacoustic detector, in accordance with the invention, is to provide an accurate and highly sensitive photoacoustic detector.

A further object of the present invention is to provide a photoacoustic detector, wherein the effect of disturbance factors resulting from external sounds on a measuring result has been reduced.

A further object of the photoacoustic detector according to a highly preferred embodiment of the present invention is to provide a method for improving the sensitivity of the photoacoustic detector and a photoacoustic detector, in which the photoacoustic detector comprises a sensor formed of a door, the sensitivity of which is improved by lowering a resonance angular frequency of the door.

A further object of the photoacoustic detector according to a highly preferred embodiment of the present invention is to provide a method for determining an optimal size of a chamber of the photoacoustic detector.

A further object of the photoacoustic detector according to a highly preferred embodiment of the present invention is to provide a highly sensitive sensor used in the photoacoustic detector and a method for optimization of the sensor.

In order to fulfill the above objects, among other things, the photoacoustic detector, the sensor for the photoacoustic detector and the method in the optimization of a door used as a sensor for the photoacoustic detector, all according to the invention, are principally characterized by what is set forth in the characterizing clauses of the independent claims.

Thus, in a typical photoacoustic detector of the present invention, the means for detecting pressure variations created in the first chamber by absorbed infrared radiation and/or light comprise at least an aperture provided in the wall of the first chamber, in association with which is provided a door adapted to be movable in response to the movement of a gas, and means for a contactless measurement of the door movement. In this context, the term contactless measurement is used in reference to measuring actions performed without one or more sensor that is attached to a door, or in a mechanical communication or contact to it, such as, for example, without a piezoelectric sensor that is attached to a surface of a door. That is, in contactless measurement, measuring means that disturb and/or suppress the movement of a door, are not attached or connected to a door. Such contactless measuring methods are, for example, different kinds of optical measuring methods. Furthermore, the above mentioned capacity measurement, in which the door of the present invention is arranged as the second sheet, is regarded as a contactless measuring method.

In a preferred photoacoustic detector according to the present invention, the door has a surface area which is at most equal to that of the aperture provided in the first chamber. In this context, the surface area of the aperture refers to a surface area of an imaginary level. The surface area of the door refers to a surface area of an azimuthal projection for a door that is projected in the imaginary level of the aperture. Thus, if the surface of the door is curved, for example, the real surface area of the door can be greater than that of the aperture, but the surface area of the azimuthal projection for a door according to the present invention is also then smaller than the surface area of the aperture.

In a preferred photoacoustic detector according to the present invention, the door is at least by one side mounted on a frame structure encircling the side faces of the door. Very advantageously, the door and the frame are fabricated from silicon, for example by forming a gap in a silicon wafer, the gap separating, excluding attachment points, the door from the rest of the wafer forming the frame.

In a preferred photoacoustic detector according to the present invention, the means for the contactless measurement of the door movement comprise: an optical measuring system, comprising at least one or more light sources for illuminating the door or a part thereof and one or more detectors for receiving light reflected from the door and for measuring the door movement as optical angular and/or translatory measurement, or a capacitive measuring system, whereby the door or a part thereof is coated with metal or the door is fabricated from an electrically highly conductive material, and which measuring system comprises a metal film or a metal-coated diaphragm set in the proximity of the door, as well as means for measuring the capacitance variations of a capacitor established by the door and the metal film. In some applications the system may comprise both optical and capacitive measuring systems. It is also possible that in addition to the optical and/or the capacitive measuring systems the photoacoustic detector comprises also other measuring systems for contactless measurement for the door movement.

In a highly preferred photoacoustic detector according to the present invention the means for the contactless measurement of the door movement are arranged in a second chamber, which constitutes a measuring space with a volume V and which is in communication with the first chamber by way of the aperture of the first chamber aperture.

In a highly preferred photoacoustic detector according to the present invention, in communication with the second chamber is further provided a third chamber which is identical to the first chamber in terms of its size and has an aperture which is identical to that included in the first chamber and connects the third chamber with the second chamber, which aperture of the third chamber is closed with a door similar to that closing the aperture of the first chamber, the movement of which door is measured in a manner similar to that used for measuring the movement of the door closing the first chamber aperture. Hence, the actual measuring signal and the reference signal can be measured separately and calculated for their amplitudes, the difference therebetween enabling an accurate filtration of external noises.

A typical sensor of a photoacoustic detector according to the present invention comprises a panel-like skirt element serving as a door frame, and a door separated from the panel-like skirt element by means of a gap. Preferably, the sensor is arrangable in communication with a chamber included in a photoacoustic detector and containing a gas to be analyzed, such that the door is moved by pressure variations created in the chamber by absorbed infrared radiation and/or light.

The sensor according to a highly preferred embodiment of the present invention does not comprise sensors fixedly mounted thereon and/or fixedly arranged in communication therewith for detecting and/or measuring the door movement.

The most important advantage of the present invention is its accuracy and sensitivity compared with typical photoacoustic detectors.

Furthermore, an advantage of the photoacoustic detector and the sensor of the photoacoustic detector according to the present invention is their simple structure and small size.

The most important advantage of the method in the optimization of a door used as a sensor for the photoacoustic detector according to the present invention is that the method is accurate and easy to apply in the optimization of the photoacoustic detector, and, especially in the optimization of the door used in it.

BRIEF DESCRIPTION OF THE DRAWING FIGURES

Figure 4B:
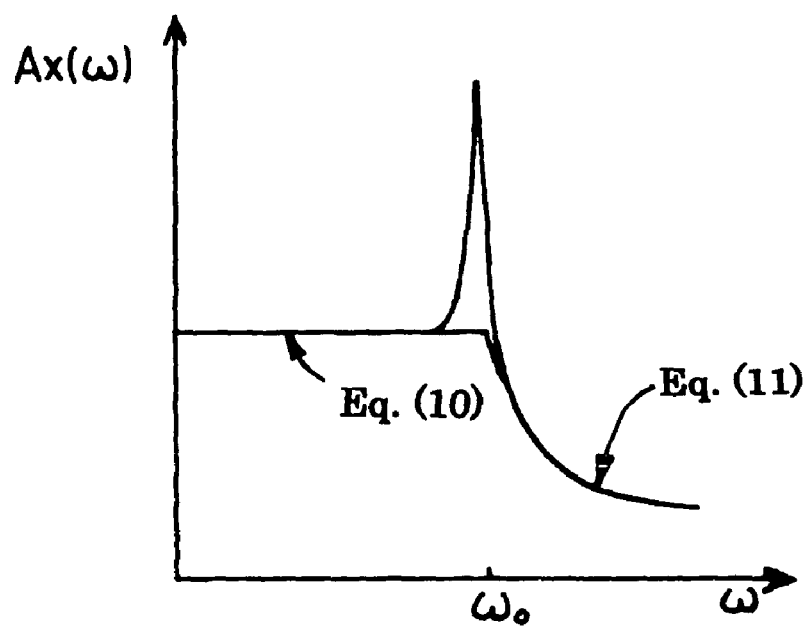
Figure 5:
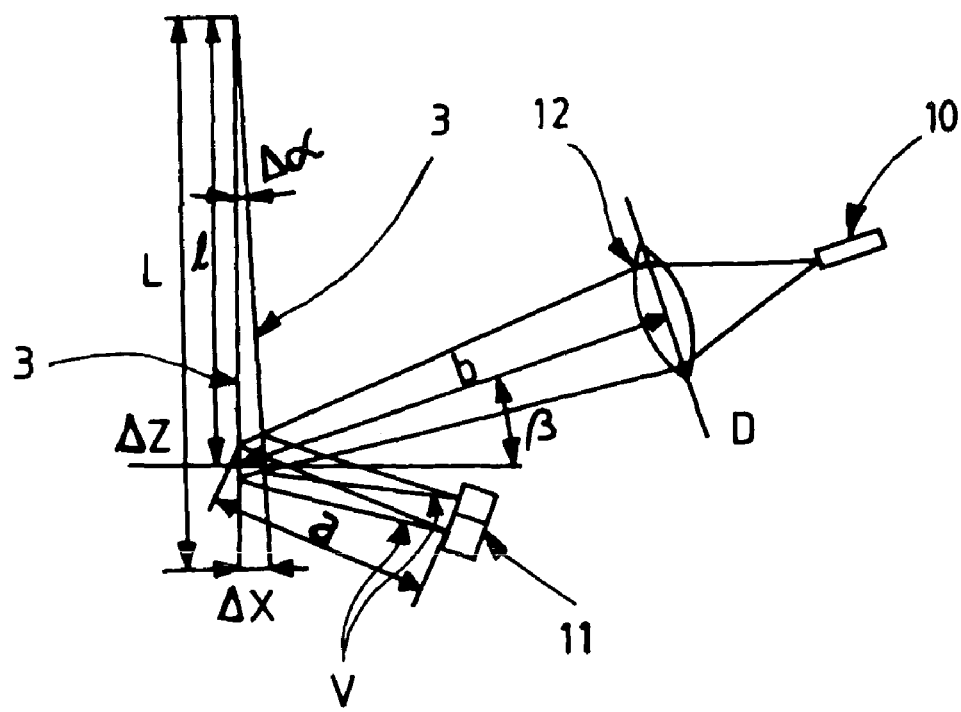
Figure 6:
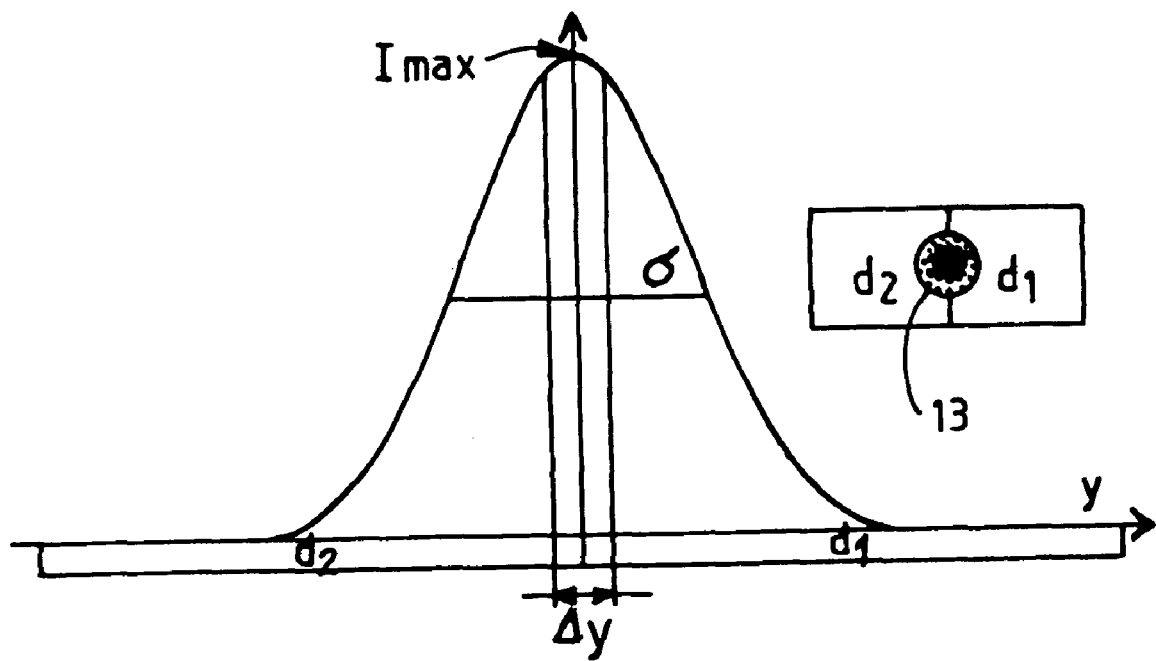
Figure 7:
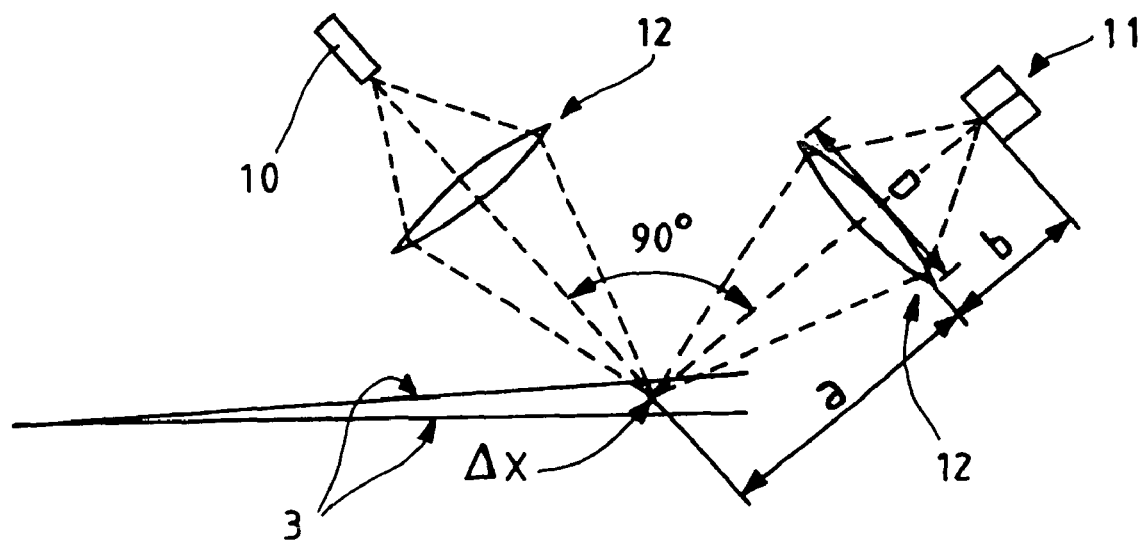
Figure 8:
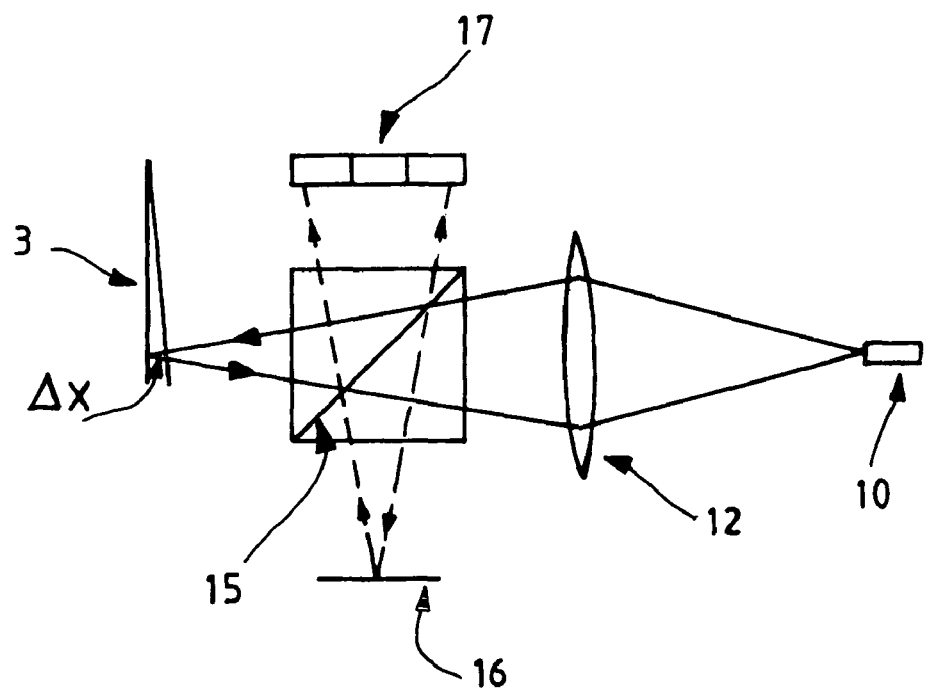
Figure 9:
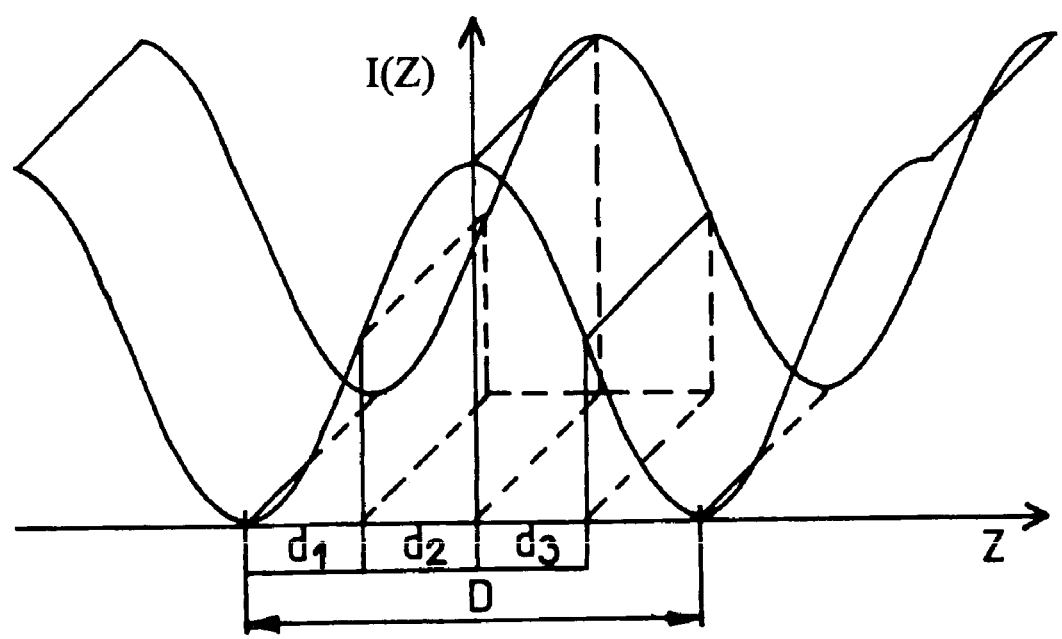
Figure 10:
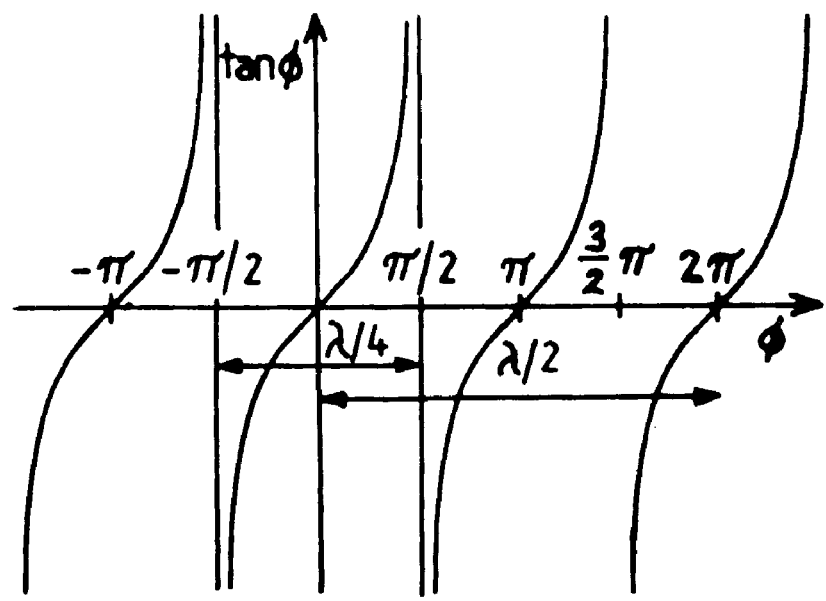

The invention will now be described in more detail with reference to the accompanying drawing, in which FIG. 1 shows schematically a design for a photoacoustic detector of the invention, FIG. 2 shows schematically a pressure sensor for a photoacoustic detector of the invention obliquely from above, FIG. 3a shows schematically a pressure sensor for a photoacoustic detector of the invention from the front, FIG. 3b shows schematically a pressure sensor for a photoacoustic detector of the invention in a cross-section, FIG. 4a shows schematically the effect of a resonance angular frequency $\omega_0$ on an amplitude $A_x(\omega)$, FIG. 4b shows schematically modeling of a door resonance, FIG. 5 shows schematically a measuring system of the present invention for the movement of a pressure sensor door on the basis of angular variation of the door, FIG. 6 shows schematically a light intensity for a double detector in the measuring system of FIG. 5, FIG. 7 shows schematically a measuring system of the present invention for the movement of a pressure sensor door on the basis of a translatory measurement of the door, FIG. 8 shows schematically a measuring system of the present invention for the movement of a pressure sensor door, based on the use of a Michelson interferometer, FIG. 9 shows schematically an interference fringe developed on a triple detector in the measuring system of FIG. 8, FIG. 10 shows schematically discontinuities in a tangent, FIG. 11 shows schematically one preferred door design for a photoacoustic detector of the present invention, FIGS. 12a and 12b show schematically a few optional door designs for a photoacoustic detector of the present invention, and FIG. 13 shows schematically a measuring system of the present invention for the movement of a pressure sensor door, by means of an optical multiplier based on multiple reflection.

DETAILED DESCRIPTION OF THE PREFERRED EMBODIMENTS

FIG. 1 shows schematically one embodiment for a photoacoustic detector of the present invention. As depicted in the figure, the photoacoustic detector comprises gas-filled chambers V and $V_0$, which contain or which can be supplied with a gas to be analyzed at a partial pressure $p_x$ and a carrier gas at a partial pressure $p_N$ (typically often nitrogen). The first chamber $V_0$ is composed of an annular housing element 1, having its first open end provided with a window 2 closing the first end of the chamber, through which infrared radiation or light in general can be guided into the chamber. The window 2 is preferably made highly transparent to infrared radiation and/or light and has preferably a thickness of about 3-6 mm. The chamber $V_0$ will be subsequently described in more detail regarding its dimensions and optimization thereof. The chamber $V_0$ has its second open end provided with a silicon door 3 closing the second end of the chamber at least partially, functioning as a pressure sensor, and having its design more closely depicted in FIGS. 2 and 3. In some special applications, the silicon door 3 can also be replaced with a microphone, a thin Mylar or metal film. Arranged as an extension to the second end of the first chamber $V_0$, the photoacoustic detector comprises a second chamber V, constituting a measuring space with a volume V. The measuring space is provided with measuring instruments for the silicon door movement. As shown in FIG. 1, the measuring space has its second end closed with a reference system, comprising a reference chamber $V_0$ which is closed at one end and identical to the first chamber $V_0$ in size. The reference chamber has its first end closed with a silicon door similar to that used for the first chamber.

FIGS. 2, 3a and 3b depict schematically and by way of example one preferred silicon-made door according to the present invention, functioning as a pressure sensor. The pressure sensor comprises a panel-like skirt member 4 serving as a door frame, and a door separated by a slit from the panel-like member. L is a width of the door, h its height, d its thickness, and $\Delta$ a width of the slot.

With low IR outputs of a light source conductible through the window into the chamber in a state of equilibrium, when $W(t)=W_{av}+W_0\cos(2\pi ft)$, there follows $$\left(\frac{dT}{dt}\right)_{T_0} = \frac{a_x p_x 2l(\cos\alpha)^{-1} W_0 \cos(2\pi ft)}{\sum_i c_V^i m_i} = \frac{a_x p_x 2l(\cos\alpha)^{-1} W_0 \cos(2\pi ft)}{V_0 \sum_i c_V^i \rho_i}, \quad (1)$$

where $a_x$ is an absorption coefficient for a gas at a partial pressure $p_x$, l is a length of the chamber, $\alpha$ is an angle between the IR beam and the centre axis of the chamber, and W(t) is a net light power proceeding into the chamber. That is, W(t) is the light intensity$\times\pi R^2$, wherein R is a radius of the chamber, $m_i$ is a mass of the gas component, $c_v^i$ is a specific heat capacity of the corresponding gas, $\rho_i$ is a density of the gas i, and $V_0$ is a volume of the smaller chamber. For example $$\sum_i c_V^i m_i = c_V^x m_x + c_V^N m_N = V_0(c_V^x \rho_x + c_V^N \rho_N).$$

It is a default in equation (1) that $\tau \ll f^{-1} \ll \tau_0$, wherein $\tau_0$ is a time constant for heat conduction out of the chamber and $\tau$ is a time constant for the conversion of absorption energy to heat.

Further $$\Delta T = T(t) - T_0 = \int \left(\frac{dT}{dI}\right)_{T_0} dI = \frac{a_x p_x 2l(\cos\alpha)^{-1} W_0 \sin(2\pi ft)}{2\pi f V_0 \sum_i c_V^i \rho_i}. \quad (2)$$

An equation of state for the ideal gas results in $$\frac{dp}{p_0} + \frac{dV}{V_0} = \frac{dT}{T_0}. \quad (3)$$

In the pressure sensor:

$$dV \approx \frac{1}{2} xA \quad (4)$$

$$A\,dp = kx = F,$$

where A represents a surface area of the pressure sensor, k is a spring constant, and x is a motion. From equations (3) and (4) is obtained $$x \approx \frac{\Delta T / T_0}{\frac{k}{Ap_0} + \frac{A}{2V_0}} \quad (\omega = 0). \quad (5)$$

Because $\Delta T$ presented in equation (2) is modulated by an angular frequency $\omega$, it is necessary to examine an equation of motion for the door (or the diaphragm), i.e.

$$m\ddot{x} - 2\beta m\dot{x} + \underbrace{m\omega_0^2 x}_{k} = F_0 e^{i\omega t} \quad (6)$$

where $F_0 e^{i\omega t}$ represents a periodic force, $\beta$ is an damping constant, $\omega_0 = \sqrt{k/m}$ is a resonance angular frequency, and x is a motion either from the end of a door or from the middle of a door or a diaphragm. The solution for equation (6)

$$x = \frac{(F_0/m) e^{i\omega t}}{\omega_0^2 - \omega^2 + 2i\omega\beta}, \quad (7)$$

from which is obtained an amplitude $$\sqrt{x * x} = A_x(\omega) = \frac{F_0/m}{\sqrt{(\omega_0^2 - \omega^2)^2 + 4\beta^2 \omega^2}}. \quad (8)$$

Equations (3) and (4) provide for amplitudes $$\frac{\Delta p}{p_0} = \frac{\Delta T}{T_0} - \frac{\Delta V}{V_0} = \frac{\Delta T}{T_0} - \frac{1}{2} A_x(\omega) \frac{A}{V_0}$$

and hence $$A_x(\omega) = \frac{A \Delta p / m}{\sqrt{(\omega_0^2 - \omega^2)^2 + 4\beta^2 \omega^2}} = \frac{A p_0 \left(\frac{\Delta T}{T_0} - \frac{A_x(\omega) A}{2V_0}\right)}{m \sqrt{(\omega_0^2 - \omega^2)^2 + 4\beta^2 \omega^2}},$$

from which $$A_x(\omega) = \frac{A p_0 \frac{\Delta T}{T_0}}{m \sqrt{(\omega_0^2 - \omega^2)^2 + 4\beta^2 \omega^2} + \frac{p_0 A^2}{2V_0}} \quad (9)$$

FIG. 4a shows schematically the effect of a resonance angular frequency $\omega_0$ on a door or diaphragm amplitude $A_x(\omega)$.

If $\omega=0$, then equation (9) results in equation (5), i.e. $A_x(0) = x$, because $m\omega_0^2 = k$.

It is preferred that the resonance of a door or a diaphragm be modelled in such a way that the increase of amplitude brought by resonance around $\omega_0$ is not taken into consideration (see FIG. 4b). That is, if $\omega < \omega_0$, the result is $$A_x(\omega) \approx \frac{A p_0 \Delta T / T_0}{m\omega_0^2 + \frac{p_0 A^2}{2V_0}} = \frac{p_0 \Delta T / T_0}{\frac{m\omega_0^2}{A} + \frac{p_0 A}{2V_0}} = \frac{p_0 \Delta T / T_0}{\rho d \omega_0^2 + \frac{p_0 A}{2V_0}}, \quad (10)$$

and if $\omega > \omega_0$, the result is $$A_x(\omega) \approx \frac{p_0 \Delta T / T_0}{\rho d \omega^2 + \frac{p_0 A}{2V_0}}, \quad (11)$$

where $\rho$ represents a door (or diaphragm) density and d is a thickness. If resonance is not utilized, it is advisable to use a door (or a diaphragm) at less than the resonance angular frequency $\omega_0$, i.e. to use equation (10), which indicates that the optimization, i.e. maximization, of amplitude $A_x(\omega)$ for door (or a diaphragm) movement must be done by means of $\omega_0$, d, $V_0$ and A. The lower $\omega_0$ and A are, the higher is $A_x(\omega)$.

Amplitude reaches a maximum, when $$\rho d \omega_0^2 + \frac{p_0 A}{2V_0}$$

reaches a minimum. This happens when $$\rho d \omega_0^2 \approx \frac{p_0 A}{2V_0} \quad (12)$$

and $$A_x^{opt}(\omega) \approx \frac{p_0 \Delta T/T_0}{2\rho d \omega_0^2} = \frac{p_0 \Delta T/T_0}{2\frac{p_0 A}{2V_0}} \quad (13)$$

By means of equations (1) and (2), the result from equation (13) is $$A_x^{opt}(\omega) \approx \frac{p_0 a_x p_x l(\cos\alpha)^{-1} W_0}{T_0 \omega V_0 \sum_i c_v^i \rho_i \rho d \omega_0^2}, \quad (14)$$

where $\omega \leq \omega_0$. The equation indicates that the best way to augment a response is to reduce angular frequencies $\omega$ and $\omega_0$. It is to be noted, that by disregarding or without optimizing the term $$\frac{p_0 A}{2V_0},$$

the best possible optimization result will not be attained. Thus, optimization can and typically should be carried out by optimizing also factors A and/or d. With typical commercially available microphones, the resonance frequency $f_0=\omega_0/2\pi$ is typically 10-20 kHz. If a microphone, whose resonance frequency $f_0=20$ kHz, is operated close to the resonance frequency, the result is $A_x^{opt}$ (20 kHz). If a similar diaphragm is used to construct a new microphone, whose resonance frequency $f_0=500$ Hz, then $$A_x^{opt}(500 \text{ Hz}) = \left(\frac{20 \text{ kHz}}{0.5 \text{ kHz}}\right)^3 A_x^{opt}(20 \text{ kHz}) = \quad (15)$$

$$40^3 \, A_x^{opt}(20 \text{ kHz}) = 64000 \, A_x^{opt}(20 \text{ kHz}),$$

provided that the microphones are optimized according to equation (12). Further, if a microphone optimized for the frequency of 500 Hz were operated at the frequency of 50 Hz, the response would further grow tenfold and the improvement factor would thus be 640000. The resonance frequency can be decreased on the basis of a subsequent equation (16) by making a door (or a diaphragm) thinner. This provides a further improvement at a ratio $d_1/d_2$ provided that the thinning of a door or a diaphragm is technically possible.

Resonance angular frequencies depend on the dimensions and material of a door (or a diaphragm). For a door $$\omega_0 = \sqrt{\frac{2E}{3\rho}} \frac{d}{L^2}, \quad (16)$$

$$A = Lh,$$

where E is a Young's modulus for the material, $\rho$ is a density, L is a width of the door, h is a height, and d is a thickness.

For a circular metal diaphragm, which is not under tension $$_E\omega_0 = \sqrt{\frac{E}{3\rho(1-\sigma^2)}} \frac{4d}{r^2}, \quad (17)$$

where $\sigma$=Poisson's ratio and r is a radius of the diaphragm.

For a tensioned thin film (for example Mylar)

$$_T\omega_0 = \frac{2.4\sqrt{T/\mu}}{r} = \frac{2.4}{r}\sqrt{\frac{F}{2\pi r\rho d}}, \quad (18)$$

where T represents a tension of the film and $\mu$ is a mass/unit area, i.e. $\mu=m/a=\rho dA/A=\rho d$.

To be exact, even for a thin film (Mylar 2 μm) applies $$\omega_{tod}^2 = {}_E\omega_0^2 + {}_T\omega_0^2, \quad (19)$$

where nevertheless $_E\omega_0^2 \ll {}_T\omega_0^2$.

If comparison is made between a door according to one exemplary embodiment of the present invention, fabricated from the same material (silicon) and having a height L/s, with a circular diaphragm not under tension, the result will be $$\frac{A_{door}^{opt}}{A_{film}^{opt}} \approx s\pi \left[\frac{8}{s\pi(1-\sigma^2)}\right]^{\frac{1}{3}} \approx 20, \quad (20)$$

if s=10, i.e. the door has a height which is one tenth of the width L.

If comparison is made between a door according to one exemplary embodiment of the present invention with a tensioned Mylar film usually employed in prior art microphones, the result will be $$\frac{A_{door}^{opt}}{A_{Mylar}^{opt}} \approx 43\left(\frac{F}{N}\right)^{\frac{2}{5}}, \quad (21)$$

where F represents a total tensile force in Newtons and s=10. The ratio is typically 10-20, depending on how little force F is required to make the film functional.

Thus, a door according to the present invention provides a solution which imparts an improvement of at least one order of magnitude in the response of a sensor. If this improvement is added to that gained by angular frequency, a low resonance door can be created which provides in a highly advantageous manner an improvement of a few million in the response of a sensor.

The use of a door-sensor according to one embodiment of the present invention requires that a slot or gap between the door and the wall be preferably made as narrow as possible.

The chamber leaks through the gap, with the result that the sensor has a lower limiting frequency $f_{cut}$, which is defined by a door gap area a as follows:

$$f_{cut} \propto v_0 \frac{a}{V_0}, \qquad (22)$$

where $v_0$ is a velocity of sound in the chamber and $V \gg V_0$.

On the other hand, it is beneficial to have a small hole between the chambers for equalizing slow pressure variations between the chambers, and which hole can thus be designed as the above-mentioned gap between the door and the door frame.

The accuracy of a photoacoustic sensor can be improved also by replacing the prior art capacitive measuring of a door (or diaphragm) movement with an optical measuring system of the present invention. Optical measuring causes very little interference with the movement of a door (or a diaphragm). According to the present invention, the movement can be measured either by means of an angle assumed by a door (or a diaphragm) or by means of a translatory movement of some point in a door (or a diaphragm).

FIG. 5 illustrates a measuring system based on angular measurement, wherein an optical indicator in the form of a laser 10 is used, while the detector is a double sensor 11. Besides a door 3, which serves as a sensor, the measuring system comprises the laser 10 as a light source, an optical lens 12 for focusing a light beam, and the double sensor 11 for receiving and measuring a light beam v reflected from the door 3. Hence, the double sensor comprises a first detector d1 and a second detector d2. The light beam v has its focus 13 at the double sensor. FIG. 6 depicts a light power of the measuring system on a double sensor, wherein at each point of y the intensity of light is integrated in a direction perpendicular to y.

In the angular measurement shown in FIGS. 5 and 6, an angle variation $\Delta\alpha$ is converted to a translatory motion $\Delta y = a2\Delta\alpha$, which is measured with a double sensor $d_1 d_2$. The angle $\Delta\alpha$ represents an average angle variation in the door area illuminated by a laser beam. Generally, $\Delta\alpha$ depends on a measuring spot, i.e. l.

$$\tan\Delta\alpha = \qquad (27)$$

$$\frac{FL^2}{6EI}\left[1-\left(\frac{L-l}{L}\right)^3\right] = \frac{8EI\Delta xL^2}{6L^3 EI}\left[1-\left(\frac{L-l}{L}\right)^3\right] = \frac{4\Delta x}{3L}\left[1-\left(\frac{L-l}{L}\right)^3\right],$$

or $$\Delta y \approx 2a\frac{4\Delta x}{3L}\left[1-\left(\frac{L-l}{L}\right)^3\right]. \qquad (28)$$

The smallest movement that can be measured with a double sensor is $$\Delta y_{min} = \frac{\sigma}{2(S/N)}, \qquad (29)$$

where $\sigma$ is the half width of a laser focus. At its minimum, $\sigma$ is limited by diffraction, i.e.

$$\sigma \approx \frac{\lambda}{D}(a+b). \qquad (30)$$

Thus, the detectable minimum movement at the end of a door is $$\Delta x_{min} \approx \frac{3L\Delta y_{min}}{8a\left[1-\left(\frac{L-l}{L}\right)^3\right]} = \qquad (31)$$

$$\frac{3L\lambda(a+b)}{2D(S/N)8a\left[1-\left(\frac{L-l}{L}\right)^3\right]} = \frac{3L\lambda(a+b)}{16aD\left[1-\left(\frac{L-l}{L}\right)^3\right](S/N)}.$$

The illuminated area at the door has a width $aD/[(a+b)\cos\beta]$, which provides a final limitation. If $b\approx 0$ and $l\approx L$, the preceding equation results in $$\Delta x_{min} \approx \frac{3L\lambda}{16D(S/N)}. \qquad (32)$$

In practice $D \leq L$, i.e.

$$\Delta x_{min} \approx \frac{3\lambda}{16(S/N)}, \qquad (33)$$

where S is a laser intensity $I_0$ and N is a sum noise of light and electronics.

The amplitude of a signal (fluctuation of light power)

$$A_v = \Delta P_{d_1} - \Delta P_{d_2} = 2\Delta y I_{max}, \qquad (34)$$

where $\Delta P_{d_1}$ and $\Delta P_{d_2}$ represent changes of light power at detectors $d_1$ and $d_2$, as well as $I_{max}$ is a maximum light power/$\Delta y$. Now, with the help of equation (28)

$$A_v = a\frac{16A_x I_{max}}{3L}\left[1-\left(\frac{L-l}{L}\right)^3\right] \approx \frac{16aA_x}{3L}\frac{P_{d_1}+P_{d_2}}{\sigma}\left[1-\left(\frac{L-l}{L}\right)^3\right], \qquad (35)$$

where $P_{d_1}+P_{d_2}=I_0$ represent the light power of a laser falling on the double sensor.

Thus, the optical indicator has a light signal whose amplitude is $$A_v = \frac{16aDI_0 A_x}{3L\lambda(a+b)} \approx \frac{16 I_0 A_x}{3\lambda}, \qquad (36)$$

where $A_x$ is the amplitude of door movement x, which must be $<\lambda$.

One of the benefits offered by an optical indicator of the present invention is its simple design, it does not interfere with door movement, and the double sensor suppresses the photon noise of laser light. Preferably, the size of a laser light spot on the door is large, $D\approx L$, in order to have a small $\sigma$. The optical indicator of the present invention can also be used for measuring a diaphragm movement, the optimal measuring site being r/√3.

Thus, according to the present invention, the door movement can also be measured in a translatory measurement. FIG. 7 depicts a measuring system of the present invention, which is not an angular measurement and by which a translatory movement x of the door can be measured. In addition to the door, the measuring system comprises a laser 10 serving as a light source, a double sensor 11, a first optical 12 lens for directing a light beam focus to the surface of a door 3 presently at rest or in stationary condition, and a second optical lens 12 for focusing on the double detector a light beam reflected from the door 3. The light source, the optical lenses and the double detector are arranged in such a way that, when the door is at rest, the angle between light beams incident on and reflecting from the door is 90 degrees. An advantage of the measurement is among other things that the laser beam is in focus at the door surface and the door may have a poor optical quality. The minimum movement that can be detected by the measuring system is $$\Delta x_{min} \approx \frac{\sqrt{2}\, a\lambda}{4D(S/N)}, \quad (37)$$

if the door has a minor surface.

The minimum movement is in the same order of magnitude as in angular measurement, i.e. $\Delta x_{min} = \lambda/(S/N)$, if $D=\sqrt{2}a/4$. Translatory measurement is also suitable for measuring a diaphragm movement, as well.

According to one preferred embodiment of the invention, the movement of a door (or a diaphragm) can also be measured optically by using an interferometer. FIG. 8 illustrates one measuring system of the present invention for measuring the movement of a door (or a diaphragm) by means of a so-called Michelson interferometer. As shown in the figure, the system comprises, in addition to the door itself, a laser 10 serving as a light source, an optical lens 12 for focusing a laser beam, a beam splitter 15 or a semi-transparent mirror for splitting the laser beam for the door and for a reference mirror 16, the reference mirror 16 and a triple sensor 17 for receiving the laser beams coming from the beam splitter 15. According to what is shown in the figure, the laser beam is approximately in focus both at the door and at the reference mirror. The reference mirror 16 is adjusted such that the triple detector 17, constituted by three sensors d1, d2 and d3, develops ¾ of the interference fringe perpendicular to the plane of paper. When x changes as the door is moving, the interference fringe moves laterally across the detectors, as shown in FIG. 9. The fringe moves across a single fringe gap, when x changes by λ/2. The intensity distribution of the fringe is $$I(z) = \frac{1}{2}A\left[1 + \cos\left(2\pi\frac{z}{D}\right)\right]. \quad (38)$$

If the interference fringe moves by ∈, signals $I_1$, $I_2$ and $I_3$ of the sensors $d_1$, $d_2$ and $d_3$ are obtained as follows:

$$I_1(\varepsilon) = \int_{\frac{2D}{4}+\varepsilon}^{\frac{D}{4}+\varepsilon} \frac{A}{2} \quad (39)$$

$$\left[1 + \cos\left(2\pi\frac{z}{D}\right)\right]dz = \frac{AD}{2\cdot 4} + \frac{AD}{2\cdot 2\pi}\left[-\cos\left(2\pi\frac{\varepsilon}{D}\right) + \sin\left(2\pi\frac{\varepsilon}{D}\right)\right],$$

$$I_2(\varepsilon) = \int_{\frac{D}{4}+\varepsilon}^{\varepsilon} \frac{A}{2}\left[1 + \cos\left(2\pi\frac{z}{D}\right)\right]dz = \quad (40)$$

$$\frac{AD}{2\cdot 4} + \frac{AD}{2\cdot 2\pi}\left[\cos\left(2\pi\frac{\varepsilon}{D}\right) + \sin\left(2\pi\frac{\varepsilon}{D}\right)\right] \text{ and}$$

$$I_3(\varepsilon) = \quad (41)$$

$$\int_{\varepsilon}^{\frac{D}{4}+\varepsilon} \frac{A}{2}\left[1 + \cos\left(2\pi\frac{z}{D}\right)\right]dz = \frac{AD}{2\cdot 4} + \frac{AD}{2\cdot 2\pi}\left[\cos\left(2\pi\frac{\varepsilon}{D}\right) - \sin\left(2\pi\frac{\varepsilon}{D}\right)\right].$$

Thus, $$\begin{cases} I_2(\varepsilon) - I_1(\varepsilon) = \frac{AD}{2\pi}\cos\left(2\pi\frac{\varepsilon}{D}\right) \\ I_2(\varepsilon) - I_3(\varepsilon) = \frac{AD}{2\pi}\sin\left(2\pi\frac{\varepsilon}{D}\right) \end{cases} \quad (42)$$

or $$\frac{2\pi\varepsilon}{D} = \tan^{-1}\left\{\frac{I_2 - I_3}{I_2 - I_1}\right\}. \quad (43)$$

Because $\varepsilon = \Delta z = 2D\Delta x/\lambda$, then $$\Delta x = \frac{\lambda}{4\pi}\tan^{-1}\left\{\frac{I_2 - I_3}{I_2 - I_1}\right\} \quad (44)$$

Since the signals $I_2-I_1$ and $I_2-I_3$ are in a 90° phase relative to each other, they can provide a way across tangent function discontinuities shown in FIG. 10. Hence, in equation $$\Delta x = \left(k + \frac{1}{2}\right)\frac{\lambda}{4} + \frac{\lambda}{4\pi}\tan^{-1}\left\{\frac{I_2 - I_3}{I_2 - I_1}\right\}$$

it is possible to measure changes ±1 of an integer k at tangent discontinuities $\phi=(n+\frac{1}{2})\pi$.

The smallest detectable movement is $$\Delta x_{min} = \frac{\sigma}{2(S/N)} = \frac{\lambda}{8(S/N)}, \quad (45)$$

where $S=I_0/2$.

If the door movement is small $<\lambda/4$, the triple sensor of the above-described measuring system can be replaced by a double sensor the same way as in the optical indicator. Thus, the combined width of the sensors is equal to the width of a single fringe and $$\begin{cases} I_1 + I_2 = \frac{AD}{2} = \frac{I_0}{2} \\ I_1 - I_2 = \frac{AD}{\pi}\sin\left(2\pi\frac{\varepsilon}{D}\right) \end{cases} \quad (46)$$

Because $\varepsilon = \Delta z = 2D\Delta x/\lambda$ is $$\Delta x = \frac{\lambda}{4\pi}\sin^{-1}\left\{\frac{I_1 - I_2}{I_1 + I_2}\right\} \approx \frac{\lambda}{8}\frac{I_1 - I_2}{I_1 + I_2} = \frac{\lambda}{4I_0}(I_1 - I_2), \quad (47)$$

where $I_0$ is the laser light power. Then, the amplitude of the light signal is $$A_l = I_1 - I_2 \approx 4\frac{I_0 A_x}{\lambda}, \quad (48)$$

where $A_x$ is the amplitude of the door movement x.

Advantages gained by interferometric measurement according to the present invention include, among other things: According to equation (44), the response is highly linear even when the movement of a door (or a diaphragm) covers several wavelengths. Absolute accuracy is high, because the shape of an interference signal is precisely consistent with $\frac{1}{2}(1+\cos(2\pi z/D))$. In addition, a laser can be focused on the measuring point of a door in an almost dot-like manner and the result is not affected by diffraction. Neither is the value of a measuring result affected by fluctuation of the laser intensity $I_0$, since the value of the maximum intensity A is reduced away in equation (44).

When comparing the optical indicator and the interferometer with each other, it can be concluded that the equation (33) does not work out in practice, because a square (rectangular) door is not the optimal form when optimizing the equation (10). That is, in other words, the optical indicator and the interferometer of the present invention function very well also with a square (rectangular) door, but should a further improvement in sensitivity and accuracy be desired, the door shape must be changed. When using a door whose height is one tenth of its width L (i.e. s=10), according to FIG. 11 the equation (31) results in $$\Delta x_{min} \approx \frac{3L\lambda}{16 L/10(S/N)} \approx \frac{2\lambda}{S/N}, \quad (49)$$

which is 16-fold with respect to the corresponding value of an interferometer (equation (45)). Further, the interferometer will be improved with respect to the optical indicator, if s grows, i.e. the door becomes shorter, which, on the other hand, also increases the amplitude $A_x(\omega)$ of door movement.

The configuration of a door can still be improved, for example by further reducing a resonance frequency by weakening a door hinge by grooving the hinge in its mid-section as shown in FIG. 12a and/or by augmenting the surface area of a door at the end of the door as shown in FIG. 12b. The door design shown in FIG. 12b is particularly suitable for the multiplier solution of an interferometer as described in more detail hereinafter. The door shown in FIG. 12b can be realized also by using more than one bar, whereby stiffness of the door increases and rotation of the door resulting in the pressure on the door diminishes. According to the present invention, the door can be realized also in such a manner, that the door, the surface area of which is smaller than the surface of the aperture, is hinged by using a long bar, whereby the structure shown in FIG. 12a, for example, can act as a bar, the door being attached to a head of the bar or formed as part of an end of the bar. An advantage of a long bar is that the use of a long bar reduces door resonance.

Since the use of an interferometer develops an almost dot-like spot on the door, it is possible to apply multiple reflection, i.e. a multiplier, in the interferometer as shown in FIG. 13. Laser light v travels to an end mirror, reflecting n times from the door 3 and from a fixed plane mirror 20, which is mounted in the vicinity of the door and preferably arranged parallel to the door surface. The laser has its focus in the proximity of the end mirror 21, from which the laser beam returns along the same path, reflecting another n times from the door. If the door nudges a distance $\Delta x$, the optical distance changes in the interferometer by $4n\Delta x$ and the response increases 2n fold, if there are no reflection losses.

If the mirrors and the door have a reflection coefficient R, the equation (45) adopts now a new form:

$$_R x_{min} = \frac{\lambda}{2nR^{4n-2}8(S/N)} = \frac{x_{min}}{2nR^{4n-2}}. \quad (50)$$

This method provides about a 10-fold augmentation of sensitivity. Multiple reflection can also be applied in a laser reflection of the present invention for translatory measurement, since the laser has its focus on the door.

When comparing an optical indicator of the present invention and an interferometer with each other, it can be concluded that both measuring systems of the present invention are capable of providing a substantial improvement regarding the accuracy and sensitivity of measurement. Interferometric measurement is even somewhat more precise than an optical indicator, but at the same time the measuring system is slightly more complicated. Hence, the required sensitivity should be considered in light of a specific application and case for selecting the appropriate measuring method.

As stated above, a problem with prior known photodetectors is disturbance caused by external sounds. According to the present invention, the effect of external sounds can be suppressed by means of a per se known double detector, which is shown in FIG. 1. According to the present invention, the actual measuring signal and a reference signal are measured separately and calculated for their amplitudes, the difference therebetween enabling a more accurate and effective filtration of external noises. Especially in a frequency range, where there is no signal developed by a gas, the interfering noise can be substantially reduced.

There is no intention whatsoever to limit the invention to the embodiment described in the foregoing disclosure, but it can be varied within the scope of the inventive concept set forth in the claims.

LITERATURE REFERENCES

[1] Nicolas Ledermann et. al., Integrated Ferroelectrics, Vol. 35, pp. 177-184 (2001)
[2] M. H. de Paula et. al., J. Appl. Phys., Vol. 64, 3722-3724 (1988)
[3] M. H. de Paula et. al., Rev. Sci. Instrum., Vol. 673, 3487-3491 (1992)

The invention claimed is:

1. A photoacoustic detector, comprising at least
   a first chamber suppliable with a gas to be analyzed,
   a window for letting modulated and/or pulsed infrared radiation and/or light in the first chamber, and
   means for detecting pressure variations created in the first chamber by absorbed infrared radiation and/or light, wherein the means for detecting pressure variations created in the first chamber by absorbed infrared radiation and/or light comprise at least
   an aperture in communication with the first chamber
   a door adapted to be movable in response to the movement of a gas, the door being positioned in the aperture and at least on one side mounted so that an inner periphery of the aperture surrounds the door and a slit exists between the door and the inner periphery of the aperture, and
   means for a contactless measurement of the door movement.

2. A photoacoustic detector as set forth in claim 1, wherein the door has a surface area which is at most equal to the area of the aperture provided in the first chamber.

3. A photoacoustic detector as set forth in claim 1, wherein the door is fabricated from silicon.

4. A photoacoustic detector as set forth in claim 1, wherein the means for a contactless measurement of the door movement comprise an optical measuring system, comprising at least one or more light sources for illuminating the door or a part thereof and one or more detectors for receiving light reflected from the door and for measuring the door movement as optical angular and/or translatory measurement.

5. A photoacoustic detector as set forth in claim 4, wherein the light source of the measuring system comprises a laser.

6. A photoacoustic detector as set forth in claim 4, wherein the detector of the measuring system comprises a double sensor.

7. A photoacoustic detector as set forth in claim 4, wherein the light source and the detector are designed as a part of an interferometer.

8. A photoacoustic detector as set forth in claim 1, wherein the means for a contactless measurement of the door movement comprise a capacitive measuring system, whereby the door or a part thereof is coated with a metal or the door is fabricated from an electrically highly conductive material, and said measuring system comprising a metal film or a metal-coated diaphragm set in the proximity of the door, as well as means for measuring the capacitance variations of a capacitor established by the door and the metal film.

9. A photoacoustic detector as set forth in claim 4, wherein the means of a contactless measurement of the door movement are provided in a second chamber, which constitutes a measuring space with a volume and which is in communication with the first chamber by way of the first chamber's aperture.

10. A photoacoustic detector as set forth in claim 9, wherein communication with the second chamber is further provided a third chamber which is identical to the first chamber in terms of size and has an aperture which is identical to that included in the first chamber and connects the third chamber with the second chamber, said aperture of the third chamber being closed with a door similar to that closing the aperture of the first chamber, the movement of said door being measured in a manner similar to that used for measuring the movement of the door closing the first chamber aperture, as well as means for calculating the amplitudes of an actual measuring signal measured from the sensor arranged in the first chamber aperture and a reference signal measured from the sensor arranged in the third chamber aperture, and for working out a difference therebetween.

11. A photoacoustic detector as set forth in claim 1, wherein the aperture is formed in a panel-like skirt element serving as a door frame, the door being on only one side mounted on structure of the door frame encircling side faces of the door.

* * * * *